United States Patent
à Wengen et al.

(10) Patent No.: US 6,830,587 B2
(45) Date of Patent: Dec. 14, 2004

(54) STIRRUP PROSTHESIS

(75) Inventors: Daniel F. à Wengen, Binningen (CH); Uwe Steinhardt, Rottenburg (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 10/621,919

(22) Filed: Jul. 17, 2003

(65) Prior Publication Data

US 2004/0064183 A1 Apr. 1, 2004

(30) Foreign Application Priority Data

Jul. 23, 2002 (DE) .................................. 202 11 102 U
Aug. 21, 2002 (DE) .................................. 202 12 771 U

(51) Int. Cl.[7] .................................................. A61F 2/18
(52) U.S. Cl. ........................................................ 623/10
(58) Field of Search ............................................ 623/10

(56) References Cited

U.S. PATENT DOCUMENTS

| 5,935,167 A | * | 8/1999 | à Wengen ..................... 623/10 |
| 6,537,199 B1 | | 3/2003 | Mueller et al. |
| 6,547,715 B1 | | 4/2003 | Mueller et al. |

* cited by examiner

Primary Examiner—David H. Willse
Assistant Examiner—Hieu Phan
(74) Attorney, Agent, or Firm—Michael J. Striker

(57) ABSTRACT

A stirrup prosthesis for implantation in a middle ear has an elastic clamping member which is displaceable on a long anvil projection and formed as a clip which is open at one side, the clip having an opening, and at least one leg with a portion extending outwardly of the opening and formed as an arch with which the prosthesis is suspendable on the long anvil projection of a human middle ear before the displacement of the prosthesis onto the long anvil projection.

8 Claims, 1 Drawing Sheet

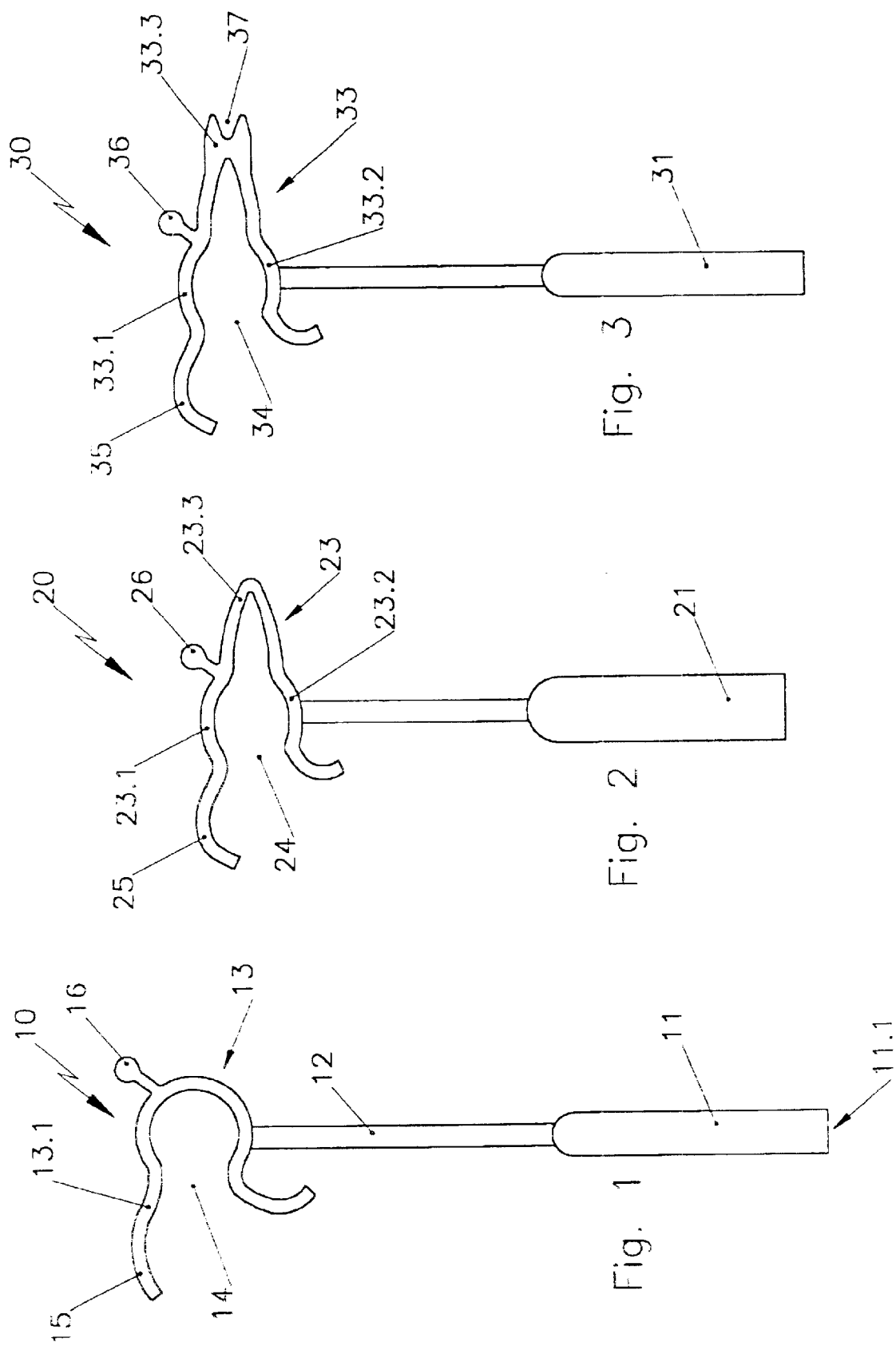

STIRRUP PROSTHESIS

BACKGROUND OF THE INVENTION

The present invention relates to a stirrup prosthesis for implantation in a middle ear.

More particularly, it relates to a stirrup prosthesis which has an elastic clamping member placeable on a long anvil projection and formed as a clip with one open side.

Such a stirrup prosthesis is disclosed in the German patent document DE 296 09 687.3. The known prosthesis can be easily implanted by simple clamping on the long anvil projection. It is held exclusively by clamping action of the clamping member. Additional mounting means are therefore no longer needed. However, during the course of implantation the prosthesis can be tilted, and therefore the operation becomes difficult for the surgeons.

SUMMARY OF THE INVENTION

Accordingly, it is an object of the present invention to provide the stirrup prosthesis of the above mentioned general type, which is improved when compared with the existing prostheses and simplifies its implantation.

In keeping with these objects and with others which will become apparent hereinafter, one feature of the present invention resides, briefly stated, in a stirrup prosthesis for implantation in a middle ear, comprising an elastic clamping member which is displaceable onto a long anvil projection and formed as a clip which is open at one side, said clip having at least one leg, said clip having an opening, and the at least one leg has a portion extending outwardly of said opening and formed as an arch with which the prosthesis is suspendable on the long anvil projection of a human middle ear before the displacement onto the anvil projection.

Since the prosthesis is suspended on the long anvil projection, the possibility is provided for an operator to exchange the operation instruments and for example to use a hook for placing the prosthesis on the long anvil projection.

The handling of the prosthesis can be also facilitated when it is provided on an outer side with a nipple for displacing the prosthesis onto the long anvil projection. The operator can engage the nipple with tweezers or a hook.

Instead of the nipple, the clip can be provided on its side which is opposite to the opening, with a notch for displacing the prosthesis on the long anvil projection. A corresponding instrument can be inserted into the notch.

Further advantages are provided when the clamping member does not completely surround the long anvil projection. Thereby the formation of a narrowing on the long anvil projection and occurrence of potential necrosis can be prevented.

It is especially advantageous when after the implantation the clamping member is arranged on the long anvil projection so that it does not abut in two regions of the periphery on the long anvil projection. Thereby, the supply vessels touch the long anvil projection only in the abutment regions. The remaining vessels extend in the both regions in which the clip does not abut against the anvil projection, so that the nutrient supply to the long anvil projection and proc. lenticularis is not endangered.

The prosthesis can be composed of a biologically compatible material. It is particularly advantageous when at least the clamping member is composed of titanium, since this material has an exceptional biocompatibility in a human middle ear.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a side view of a prosthesis in accordance with a first embodiment of the present invention;

FIG. 2 is a side view of a prosthesis in accordance with a second embodiment of the present invention; and FIG. 3 is a side view of a prosthesis in accordance with a third embodiment of the present invention.

DESCRIPTION OF THE PREFERRED EMBODIMENTS

A stirrup prosthesis shown in FIG. 1 is identified as a whole with reference numeral 10. It includes a plunger-shaped part 11 which has a lower end side 11.1 formed to sit in an oval window and thereby to transmit the sound to an inner ear. A prosthesis shaft 12 is connected to the upper end of the plunger-shaped part 11. A clamping member, in the form of a clip 13, is provided at the upper end of the prosthesis shaft 12 and composed of an elastic material. The clip 13 is open at its one side.

The clip 13 has an opening 14, with which it can be moved over the long anvil projection. The clip 13 has an upper leg 13.1 which is elongated outwardly beyond the opening 14 and forms an arch 15. The whole prosthesis 10 can be suspended by the arch 15 on the long anvil projection. For facilitating the displacement, a nipple 16 is arranged on the outer side of the clip 13. The operator can engage the nipple 16 for example with a tweezer or a hook and to displace the prosthesis.

As can be seen from FIG. 1, the prosthesis 10 shown in this drawing has the clip 13 which is formed so that it surrounds three fourth of the circumference of the anvil projection.

FIG. 2 is a view showing a prosthesis in accordance with a second embodiment of the present invention. The prosthesis is identified as a whole with reference numeral 20 and has a clamping member 23 which is in contact with the long anvil projection only in two regions 23.1 and 23.2. The region 23.3 which is located between the regions 23.1 and 23.2 extends at a relatively great distance from the anvil projection. Therefore the supply vessels of the long anvil projection can not be narrowed by the clamping member 23. Otherwise, the clamping member 23 is formed similarly to the clamping member 13 of the first embodiment of the present invention.

In the prosthesis 20 the upper leg also has an arch-shaped portion 25, with which the prosthesis 20 can be suspended on the long anvil projection. Moreover, a nipple is provided on the outer side of the clamping member 23 for placement of an operation instrument.

FIG. 3 shows a prosthesis in accordance with a third embodiment of the present invention. The prosthesis is identified as a whole with reference numeral 30 and has a clamping member 33 which is formed similarly to the clamping member 23 of the embodiment shown in FIG. 2. In addition to the nipple 36, a notch 37 is provided in the region 33.3 of the clamping member 33 which is opposite to the opening 34. The notch 37 is formed so that an operation tool can be inserted into it, for displacement of the prosthesis 30 onto the long anvil projection.

The prostheses 10, 20, 30 differ from one another also in their length and also in the thickness of the plunger-shaped parts 11, 21, 31.

It will be understood that each of the elements described above, or two or more together, may also find a useful application in other types of constructions differing from the types described above.

While the invention has been illustrated and described as embodied in stirrup prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A stirrup prosthesis for implantation in a middle ear, comprising an elastic clamping member which is displaceable on a long anvil projection and formed as a clip which is open at one side, said clip having an opening, and at least one leg with a portion extending outwardly of said opening and beyond that opening and said portion being formed as an arch with which the prosthesis is suspendable on the long anvil projection of a human ear before displacement of the prosthesis onto the long anvil projection.

2. A stirrup prosthesis as defined in claim 1, wherein said clip on its outer side is provided with a nipple for displacing the prosthesis onto the long anvil projection.

3. A stirrup prosthesis as defined in claim 1, wherein said clamping member on its side which is opposite to said opening is provided with a notch for displacement of the prosthesis onto the long anvil projection.

4. A stirrup prosthesis as defined in claim 1, wherein said clamping member is formed so that it does not completely surround the long anvil projection.

5. A stirrup prosthesis as defined in claim 1, wherein said clamping member is formed so that after implantation said clip is arranged on the long anvil projection so that it does not abut against the long anvil projection in two regions over a periphery.

6. A stirrup prosthesis as defined in claim 1, wherein said clamping member is composed of titanium.

7. A stirrup prosthesis for implantation in a middle ear, comprising an elastic clamping member which is displaceable on a long anvil projection and formed as a clip which is open at one side, said clip having an opening, and at least one leg with a portion extending outwardly of said opening and formed as an arch with which the prosthesis is suspendable on the long anvil projection of a human ear before displacement of the prosthesis onto the long anvil projection, wherein said clip on its outer side is provided with a nipple for displacing the prosthesis onto the long anvil projection.

8. A stirrup prosthesis for implantation in a middle ear, comprising an elastic clamping member which is displaceable on a long anvil projection and formed as a clip which is open at one side, said clip having an opening, and at least one leg with a portion extending outwardly of said opening and formed as an arch with which the prosthesis is suspendable on the long anvil projection of a human ear before displacement of the prosthesis onto the long anvil projection, wherein said clamping member on its side which is opposite to said opening is provided with a notch for displacement of the prosthesis onto the long anvil projection.

* * * * *